United States Patent [19]

Abe et al.

[11] Patent Number: 4,636,144

[45] Date of Patent: Jan. 13, 1987

[54] MICRO-FEED PUMP FOR AN ARTIFICIAL PANCREAS

[75] Inventors: Hiroshi Abe, Nishinomiya; Motoaki Shichiri, Osaka; Ryuzo Kawamori, Kobe; Tasuku Ichoh, Suita; Kenji Iwatani, Takatsuki; Mamoru Higuchi, Suita; Kiyotaka Takagi, Kyoto; Norihiko Okamoto, Ikeda; Toshiyuki Okudaira, Osaka, all of Japan

[73] Assignee: Fujisawa Pharmaceutical Co., Ltd., Osaka, Japan

[21] Appl. No.: 847,114

[22] Filed: Apr. 3, 1986

Related U.S. Application Data

[63] Continuation of Ser. No. 704,016, Feb. 21, 1985, abandoned, which is a continuation of Ser. No. 508,910, Jun. 29, 1983, Pat. No. 4,515,584.

[30] Foreign Application Priority Data

Jul. 6, 1982 [JP] Japan .................................. 57-118114
Jul. 9, 1982 [JP] Japan .................................. 57-120078

[51] Int. Cl.$^4$ ........................ F04B 43/12; F04B 21/00; A61M 5/00
[52] U.S. Cl. ..................................... 417/63; 417/475; 417/477; 604/153
[58] Field of Search ........................ 417/63, 475–477; 604/67, 153; 128/DIG. 12

[56] References Cited

U.S. PATENT DOCUMENTS 3,140,666  7/1965  Currie .................................. 417/477
3,172,367  3/1965  Kling .............................. 417/477 X
4,206,755  6/1980  Klein .................................. 128/214 E
4,315,718  2/1982  Hogan .................................. 417/477
4,385,630  5/1983  Gilcher et al. .................... 604/67 A
4,424,011  1/1984  O'Brien et al. ...................... 417/477

FOREIGN PATENT DOCUMENTS

0039044   4/1981  European Pat. Off. .
2326265  12/1974  Fed. Rep. of Germany .
2817363  10/1979  Fed. Rep. of Germany .
81/01794  7/1981  PCT Int'l Appl. .
2102503   2/1983  United Kingdom .................. 417/63

Primary Examiner—John J. Vrablik
Attorney, Agent, or Firm—Oblon, Fisher, Spivak, McClelland, & Maier

[57] ABSTRACT

An artificial pancreas includes a blood sugar determination unit for measuring the blood sugar of the living body, an injection unit including a container for a blood sugar control agent and a feed pump for the control agent and adapted to inject the control agent into the living body and an arithmetic control unit for calculating the dose of the control agent and controlling the pump of the injection unit in accordance with the results of the calculation. The pump includes a disc-shaped roller holder which holds a plurality of rollers around its periphery. Each roller includes flanges at opposite ends. An elastic tube extends around the rollers under tension. Magnets are embedded along the periphery of the roller supports and are sensed to determine the amount of pumping which has occurred. Tubular stoppers are provided within stepped grooves in the pump housing to receive the ends of the elastic tubes.

1 Claim, 13 Drawing Figures

MICRO-FEED PUMP FOR AN ARTIFICIAL PANCREAS

This application is a continuation of application Ser. No. 704,016, filed Feb. 21, 1985, now abandoned, which is a continuation of application Ser. No. 508,910, filed June 29, 1983, now U.S. Pat. No. 4,515,584.

BACKGROUND OF THE INVENTION

The present invention relates to an artifical pancreas, and more particularly to an artificial pancreas having the function of measuring blood sugar values (blood glucose concentrations) of the living body and injecting blood sugar control agents into the living body in accordance with the measurements.

Blood sugar control agents include hypoglycemic agents and hyperglycemic agents. Examples of hypoglycemic agents are insulin, etc., while exemplary of hyperglycemic agents are glucagon, glucose, etc.

Such artificial pancreas heretofore known include those of the so-called bedside type which comprise a blood sugar determination unit for measuring the blood sugar of the living body, an injection unit having an insulin container, a glucagon container, an insulin feed pump and a glucagon feed pump for injecting insulin or glucagon into the living body, an arithmetic control unit for calculating the dose of insulin or glucagon based on the measurement and controlling the pump concerned of the injection unit in accordance with the result of calculation, and a case housing these units. However, the conventional artificial pancreas of the bedside type has the drawback of being large-sized and limited to bedside use because the blood sugar measuring electrodes (sensor) of the blood sugar determination unit, the feed pumps of the injection unit and the arithmetic control unit are relatively large. Further because the blood sugar determination unit is adapted to determine blood sugar with use of blood collected from the patient and diluted, the collection of blood heavily burdens the patient, so that it is impossible to use the device continually for a long period of time.

SUMMARY OF THE INVENTION

An object of the present invention is to provide an artificial pancreas which is small-sized in its entirety.

Another object of the present invention is to eliminate the need to collect the blood for the determination of blood sugar and to provide an artificial pancreas which is usable continually for a prolonged period of time.

The artificial pancreas of the present invention comprises a blood sugar determination unit for measuring the blood sugar of the living body, an injection unit including a container for a blood sugar control agent and a feed pump for the control agent and adapted to inject the control agent into the living body, and an arithmetic control unit for calculating the dose of the control agent based on the blood sugar measurement and controlling the pump of the injection unit in accordance with the result of calculation. The artificial pancreas is characterized in that the blood sugar determination unit has electrode means to be inserted into the living body for measuring the blood sugar, the feed pump comprising a plurality of rollers rotatably mounted on a rotatable roller holder along the outer periphery of the holder and an elastic tube having an intermediate portion reeved around some of the rollers under tension, the arithmetic control unit having a microcomputer.

With the artificial pancreas of the present invention, there is no need to collect the blood for the determination of blood sugar since the blood sugar determination unit is provided with the measuring electrode means to be inserted into the living body. This lessens the burden on the patient, rendering the device usable for a long period of time. The measuring electrode means need not be encased, while the feed pump comprises rollers mounted on a rotatable roller holder and arranged along the outer periphery of the holder and an elastic tube reeved around the rollers at its intermediate portion as tensioned, and the control unit comprises a microcomputer, so that the injection unit and the control unit can be small-sized. Thus the device can be compacted in its entirety and is therefore not limited to bedside use but is portable for use.

Other features of the present invention will become apparent from the following description.

DESCRIPTION OF THE PREFERRED EMBODIMENTS

Figure 1:
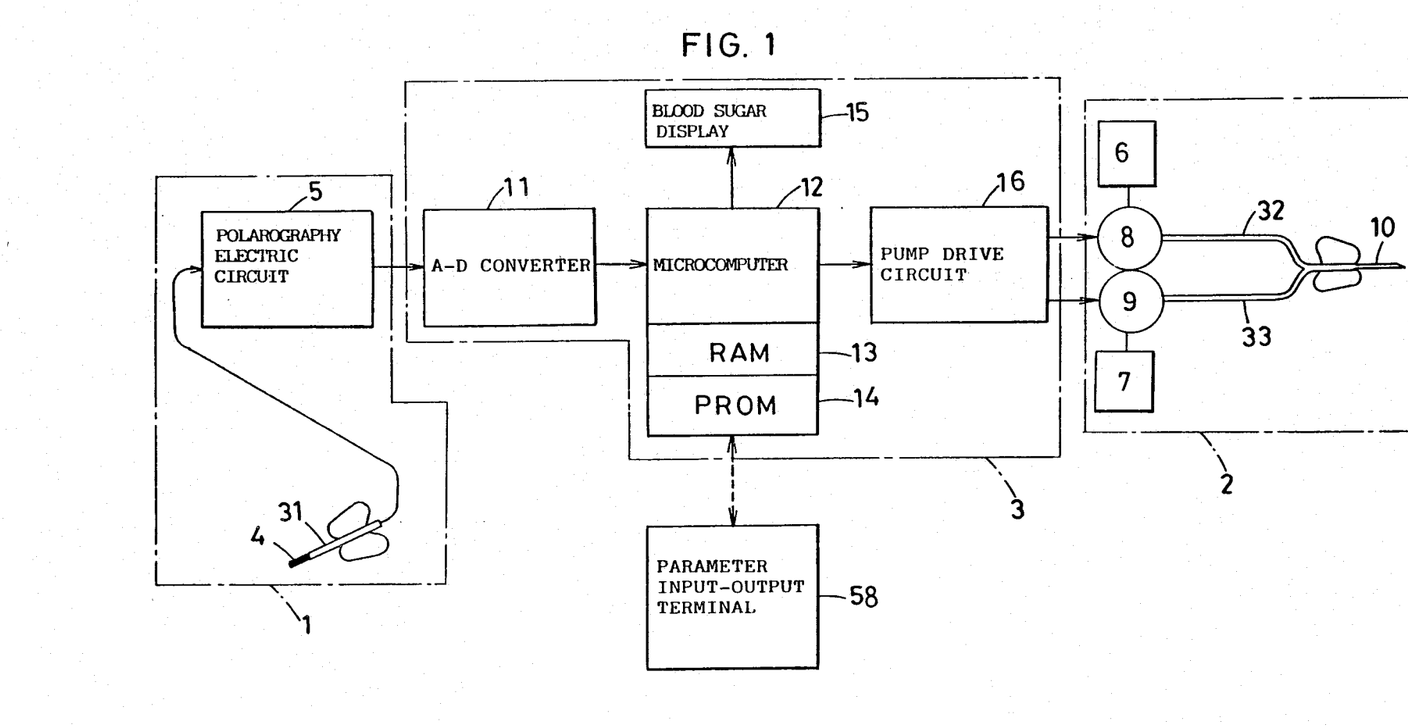
FIG. 1 is a block diagram showing a first embodiment of the invention in its entirety.
Figure 2:
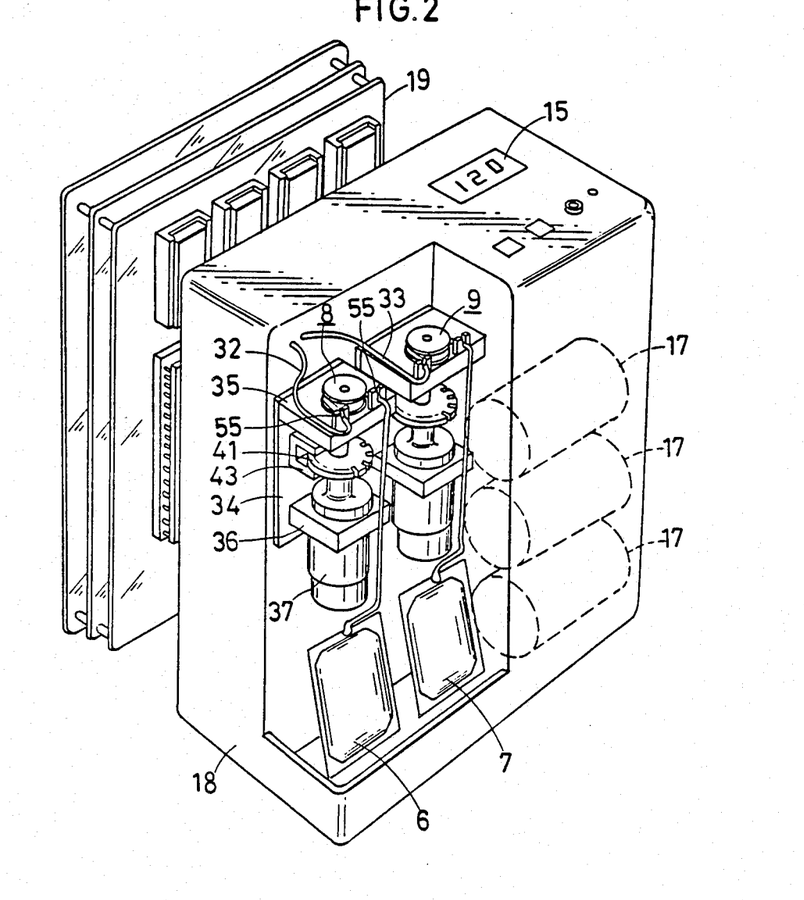
FIG. 2 is an exploded perspective view showing main components.

FIG. 1 shows an artificial pancreas comprising a blood sugar determination unit 1, an injection unit 2, and an arithmetic control unit 3. The determination unit 1 comprises electrode means 4 for measuring blood sugar values by polarography, and a polarography electric circuit 5. The injection unit 2 includes an insulin conainer 6, a glucagon container 7, an insulin feed pump 8, a glucagon feed pump 9 and an injection needle 10. The arithmetic control unit 3 includes an A-D converter 11, a microcomputer 12, a random access memory (RAM) 13, a programmable read-only memory (PROM) 14, a blood sugar display 15 and a pump drive circuit 16. As seen in FIG. 2, the two containers 6, 7, two pumps 8, 9, blood sugar display 15 and power supply dry batteries 17 are housed in a small casing 18. The polarography electric circuit 5, A-D converter 11, microcomputer 12, RAM 13, PROM 14 and pump drive circuit 16 are mounted on a printed circuit board 19 housed in the casing 18.

Figure 3:
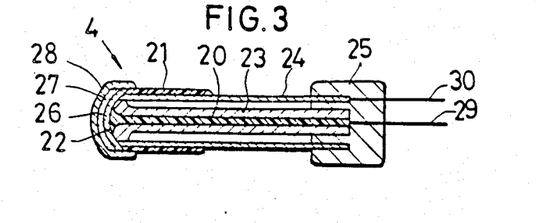
FIG. 3 is a view in longitudinal section showing electrodes for measuring blood sugar values.

The electrode means 4 is adapted to measure blood glucose concentrations based on current resulting from the electrolysis of hydrogen peroxide which is produced from glucose in the presence glucose oxidase serving as a catalyst. As seen in FIG. 3 in greater detail, the electrode means 4 comprises a platinum electrode (anode) 20 and a silver electrode (cathode) 21. The platinum electrode 20 is insulated with glass 23 except at its front end 22 serving as an electrode reaction portion and at its rear end serving as a lead wire connecting portion. The platinum electrode 20 is inserted in a stainless steel cylinder 24 having the silver electrode 21 formed over its outer surface. The front ends of the platinum electrode 20 and the cylinder 24 are fixed together by thermally adhering the front end of the glass insulator 23 to the front end of the cylinder 24. The rear ends of the platinum electrode 20 and the cylinder 24 are fixed together by a plastic plug 25 fitting over these rear ends. A cellulose acetate film 26 serving as a hydrophilic semipermeable membrane which is permeable to hydrogen peroxide is laminated to the surface of the front end 22 of the platinum electrode 20, with an immobilized glucose oxidase membrane 27 further laminated to the outer surface of the film 26. A polyurethane film 28 serving as a hydrophilic semipermeable membrane which is permeable to glucose, oxygen and hydrogen peroxide is laminated to the membrane 27. The platinum electrode 20 and the cylinder 24 are connected, at their rear ends, to insulated lead wires 29 and 30, respectively. The measuring electrode means 4 is attached to the forward end of a catheter 31 to be lodged in vivo and is inserted into the blood vessel or beneath the skin. The signal from the electrode means 4 is fed to the polarography electric circuit 5 through the catheter 31. The circuit 5 applies a predetermined voltage across the electrodes 20 and 21 to measure the current resulting from the electrolysis of hydrogen peroxide and amplifies the current. The amplified current value is fed to the A-D converter 11, and the blood glucose concentration, i.e., blood sugar value, is determined based on the value.

Figure 4:
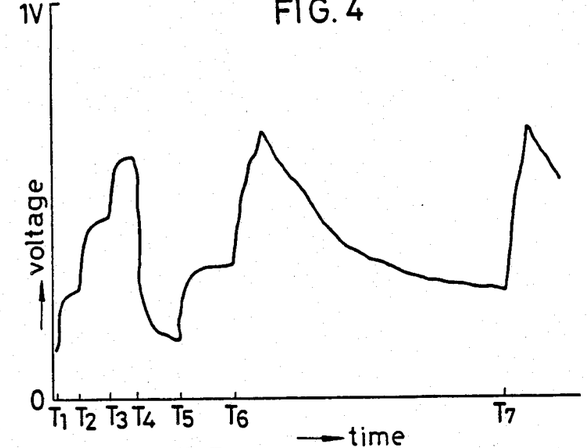
FIG. 4 is a graph showing the result of a glucose loading test conducted on canine blood with use of the electrode means of FIG. 3.
Figures 5, 6:
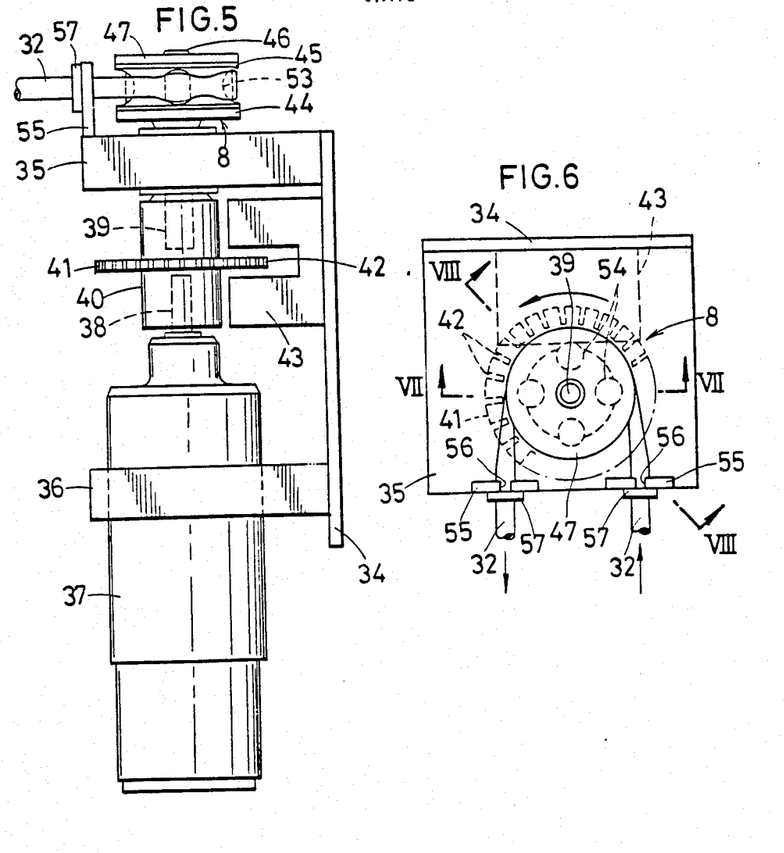
FIG. 5 is a side elevation showing a feed pump.
FIG. 6 is a plan view of the same.
Figure 7:
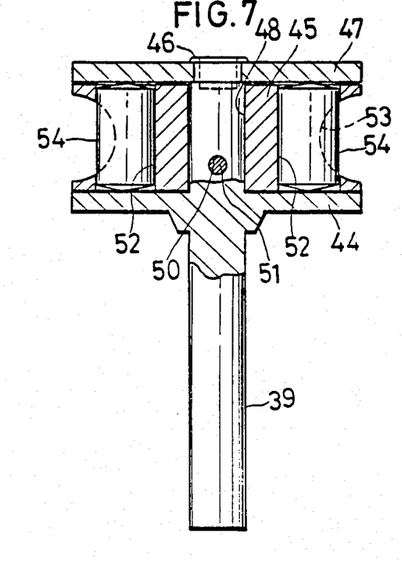
FIG. 7 is an enlarged fragmentary view in section taken along the line VII—VII in FIG. 6.
Figure 8:
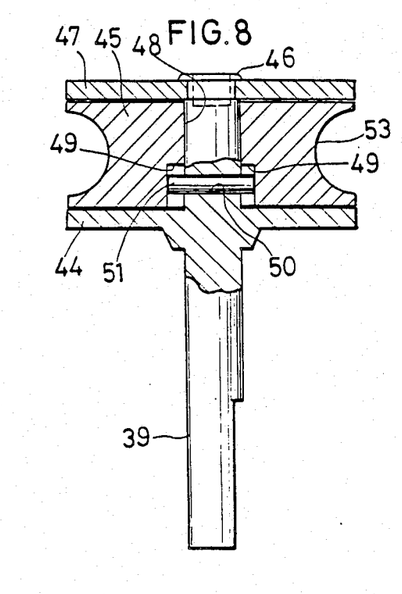
FIG. 8 is an enlarged fragmentary view in section taken along the line VIII—VIII in FIG. 6.
Figure 9:
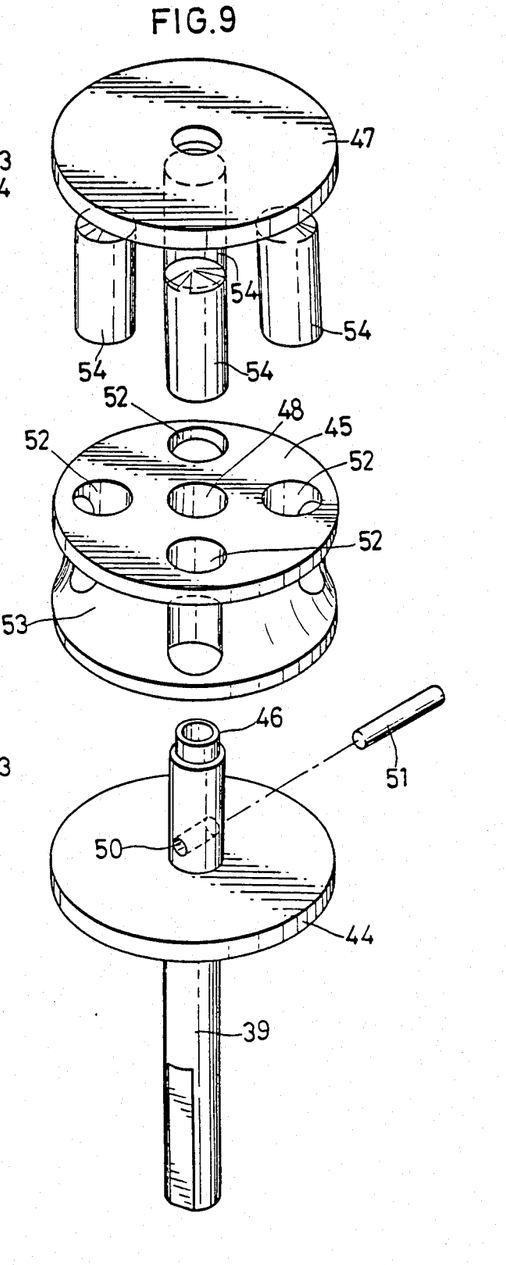
FIG. 9 is an exploded perspective view showing the main components of the feed pump.

FIG. 4 shows the result of a glucose loading test conducted on canine blood with use of the electrode means 4. The measurements well coincides with those obtained by the standard determination method generally practiced at present. With reference to FIG. 4, the time is plotted as abscissa vs. the voltage as ordinate. The electrode means is exposed to standard test solutions of 100 mg/dl from T1 to T2, of 200 mg/dl from T2 to T3 and of 300 mg/dl from T3 to T4, to physiological saline from T4 to T5, and to normal canine blood from T5 to T6. From T6 to T7, 5 cc of 50% aqueous glucose solution is intravenously given to the thigh of the dog.

Further the results of basic experiments have revealed that the electrode means 4 operates stably in vitro systems for more than 24 hours, exhibiting linear characteristics in response reaction at glucose concentrations of 0 to 500 mg/dl, a short response time of the order of seconds and good stability at temperatures of 36° to 42° C. In vivo animal experiments have demonstrated that the electrode means exhibits good responsiveness to the load of glucose and insulin hypoglycemia. Thus it has been ascertained that the electrode means affords highly reliable measurements.

The components of the measuring electrode means 4 can also be made of suitable materials other than those mentioned above, while it is preferable to use platinum, gold or like noble metal for the anode and to use silver, silver chloride or the like for the cathode. Preferred materials for the insulator are glass, plastics, etc. Cellulose derivatives such as cellulose mono-, di- or triacetate, cellulose propionate and cellulose butyrate are desirable for forming the hydrophilic semipermeable membrane which is permeable to hydrogen peroxide. The carrier for immobilizing glucose oxidase is preferably porous glass or plastics. It is desirable to incorporate heparin or like anticoagulant into the hydrophilic semipermeable membrane permeable to glucose, oxygen and hydrogen peroxide for the prevention of blood coagulation on the surface of the electrode means. Glucose oxidase may be immobilized and laminated by repeating the procedure of immersing the front end of the electrode means in a glucose oxidase-containing liquid and drying. To render the electrode means flexible, a plastic tube may be used instead of the stainless steel cylinder 24. In this case, the cathode can be formed by forming a silver film on the outer surface of the plastic tube by vacuum evaporation and further plating the film with silver.

The two containers 6 and 7 are made of a flexible material, such as vinyl chloride film or sheet. They are made by folding a rectangular sheet of flexible material in two or superposing two rectangular sheets of flexible material and sealing edge portions of the double sheet in the form of a bag. The insulin container 6 is filled with insulin, and the glucagon container 7 with glucagon. Liquid feeding elastic tubes 32, 33 are connected, each at its one end, to the containers 32, 33. The two tubes 32, 33 extend outward from the casing 18 and are connected to the single injection needle 10 at the other ends thereof.

FIGS. 5 to 9 show the insulin feed pump 8 in greater detail. A pump support plate 34 fixed vertically to the casing 18 is fixedly provided one one side thereof with a horizontal bracket 35 and another horizontal bracket 36 positioned below and opposed to the bracket 35. A d.c. motor 37 equipped with a reduction gear and oriented upward is fixed to the lower bracket 36. A vertical rotary shaft 39 coaxial with the motor shaft 38 is rotatably supported at an intermediate portion by the upper bracket 35. The motor shaft 38 and the rotary shaft 39 are connected to each other by a coupling 40. A rotary disk 41 fixed horizontally to the coupling 40 has 24 cutouts 42 formed in its circular outer peripheral portion and arranged equidistantly. Mounted on an upper portion of the support plate 34 on one side thereof is a photoelectric rotational angle sensor 43 comprising a light-emitting element and a photocell arranged above and below the peripheral portion of the disk 41. A roller retainer 44 in the form of a horizontal disk and positioned immediately above the upper bracket 35 is integral with the rotary shaft 39. A roller holder 45 in the form of a short solid cylinder is fitted to the portion of the rotary shaft 39 above the retainer 44. The upper end of the rotary shaft 39 projecting upward beyond the roller holder 45 is in the form of a hollow cylinder 46 having a thin wall and slightly smaller diameter than the other shaft portion. A disk-like roller retainer 47 is fitted around the cylindrical portion 46 and secured to the rotary shaft 39 by enlarging the upper end of the cylindrical portion 46 outward. The roller holder 45 is made of polytetrafluoroethylene and formed in the center of its bottom with a groove 49 extending diametrically slightly beyond opposite sides of the rotary shaft inserting bore 48. A horizontal bore 50 extending through the rotary shaft 39 is formed in the portion thereof corresponding to the groove 49. A horizontal pin 51 is inserted through the bore 50. Opposite ends of the pin 51 projecting from the rotary shaft 39 fit in the groove 49. The rotation of the rotary shaft 39 is delivered to the roller holder 45 by the pin 51. Four circular bores 52 extending through the roller holder 45 vertically are equidistantly arranged on a circumference centered about the rotary shaft 39. The roller holder 45 has an annular tube guide groove 53 having a semicircular cross section, formed in its outer peripheral side surface over the entire circumference thereof and partly positioned in the bores 52. A solid cylindrical roller 54 having an outside diameter slightly smaller than the inside diameter of the circular bore 52 is rotatably fitted in each bore 52. The outer periphery of the roller 54 is partly positioned in the guide groove 53. Each of the upper and lower ends of the roller 54 is in the form of a cone having a very small height. The length of the roller 54 is slightly smaller than the distance between the upper and lower roller retainers 47 and 44. The roller 54 is substantially immovable axially thereof. The rotary shaft 39, the roller retainer 47 and the rollers 54 are made of stainless steel. The intermediate portion of the liquid feeding elastic tube 32 connected to the insulin container 6 is reeved around the portions, positioned within the guide groove 53, of the rollers 54 disposed in the range of about 180° about the center of the roller holder 45 and is tensioned, in the following manner. Two tube holding plates 55 are fixed to the upper side of one end of the upper bracket 35, with a U-shaped cutout 56 formed in the upper portion of each plate 55. On the other hand, the intermediate portion of the tube 32 has two annular stoppers 57 spaced apart, secured to the tube by suitable means as by adhesion and having a larger outside diameter than the tube 32. The tube portion between the stoppers 57 is reeved around the rollers 54, the tube 32 is pulled, and the portions of tube adjacent the stoppers 57 and positioned closer to the rollers 54 are inserted into the cutouts 56 of the holding plates 55, with the stoppers 57 in pressing contact with the plates 55, whereby the tube 32 is reeved around the rollers 54 under predetermined tension. By the rotation of the roller holder 45 in the direction of arrow shown in FIG. 6, insulin is supplied from the container 6 to the needle 10 through the tube 32 as indicated by arrows in FIG. 6. The amount of supply is in proportion to the angle of rotation of the pump 8, i.e., the roller holder 45.

The glucagon feed pump 9 also has the same construction as above.

The PROM 14 of the arithmetic control unit 3 has stored therein a program for calculating doses of insulin and glucagon based on the measurements of blood sugar and controlling the pumps 8 and 9 of the injection unit 2 in accordance with the result of calculation. The parameters, measuring data, etc. for the calculation formula are stored in the RAM 13. Such parameters differ with the body weight of the patient, the concentration of insulin, etc. and are set with use of a parameter input-output terminal 58. The terminal 58 is provided with a keyboard, printer, display and the like and is connected to the artificial pancreas only when setting the parameters but is separated therefrom while the artificial pancreas is in use.

When the artificial pancreas is to be used, the casing 18 is attached to the garment or the like of the patient. It is used with the electrode means 4 inserted in the blood vessel or beneath the skin and with the injection needle 10 inserted into the blood vessel or beneath the skin. Blood sugar is measured at a specified time interval (e.g. every minute), and the doses, i.e., the amounts of insulin and glucagon to be injected, are calculated based on the measurements. The required amount of insulin or glucagon is injected.

Figure 10:
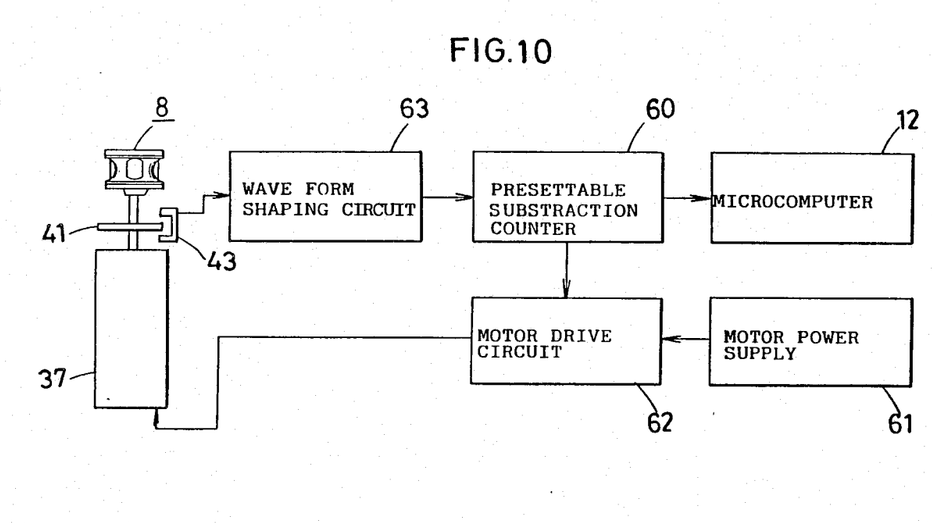
FIG. 10 is a block diagram showing the main construction of a pump drive circuit.

More specifically stated, the analog signal from the electrode means 4 is amplified by the polarography electric circuit 5 and then converted by the A-D converter 11 to a digital signal, which is fed to the microcomputer 12. At a given time interval, the microcomputer 12 calculates the blood sugar value based on the digital signal and further calculates the doses of insulin and glucagon based on the result. The method of calculation, which is the same as is practiced in conventional bedside artificial pancreas devices, will not be described. At least one of the doses of insulin and glucagon thus obtained is zero; only one of insulin and glucagon or neither of them is administered in accordance with the blood sugar level. When there is a need to inject insulin or glucagon, the microcomputer 12 calculates the angle of rotation of the pump 8 or 9 corresponding to the amount to be injected, i.e., dose, giving instructions to the pump drive circuit 16 as to the pump to be driven and the rotational angle. FIG. 10 shows the main construction of the pump drive circuit 16. For example when insulin is to be injected, the pump 8 is rotated only through the angle instructed by the microcomputer 12 in the following manner. The rotational angle instruction is given by the microcomputer 12 in terms of the number of pitches of the cutouts 42 in the rotary disk, one pitch (15°) being one unit, and the instruction value is set on a presettable subtraction counter 60. For example when the pump 8 needs to be rotated one turn, an instruction value of 24 is set on the counter 60, whereupon a motor drive circuit 62 extending from a motor power supply 61 to the motor 37 is closed to start the pump 8, permitting the disk 41 to rotate with the pump 8. Every time the pump 8, i.e., the disk 41, rotates by one pitch of cutout 42, the rotational angle sensor 43 feeds a signal to the counter 60 via a wave form shaping circuit. Every time such a signal is given, 1 is subtracted from the contents of the counter 60. While the contents of the counter 60 remain positive, the pump 8 continues rotation. Upon the reduction of the contents of the counter 60 to zero, the motor drive circuit 62 opens to stop the pump 8. In this way, the pump 8 rotates by an amount corresponding to the instruction value given by the microcomputer 12, whereby a specified quantity of insulin in proportion to that amount is infused or given subcutaneously from the container 6 via the tube 32 and needle 10. Glucagon is administered in the same manner as above.

The measuring electrode means to be inserted into the living body is not limited to the one included in the above embodiment but can be modified suitably.

The feed pump of the foregoing embodiment can be made smaller than the conventional one, composed of a smaller number of parts and fabricated less expensively because the rollers are fitted in the circular bores of the roller holder without the necessity of being supported by roller bearings. Further because the elastic tube is reeved around the portions of the rollers positioned in a guide groove which is formed in the outer peripheral side surface of the holder and partly positioned in, or sharing the same space as, the circular bores, the tube can be effectively prevented from zigzagging and thereby given a prolonged life without the need to use rollers of special shape or tube guides conventionally employed. The d.c. motor used for the feed pump of the foregoing embodiment has the advantage of being lesser in power consumption than pulse motors. However, the feed pump and the pump drive circuit are not limited in construction to those of the embodiment but can be modified suitably.

Figure 11:
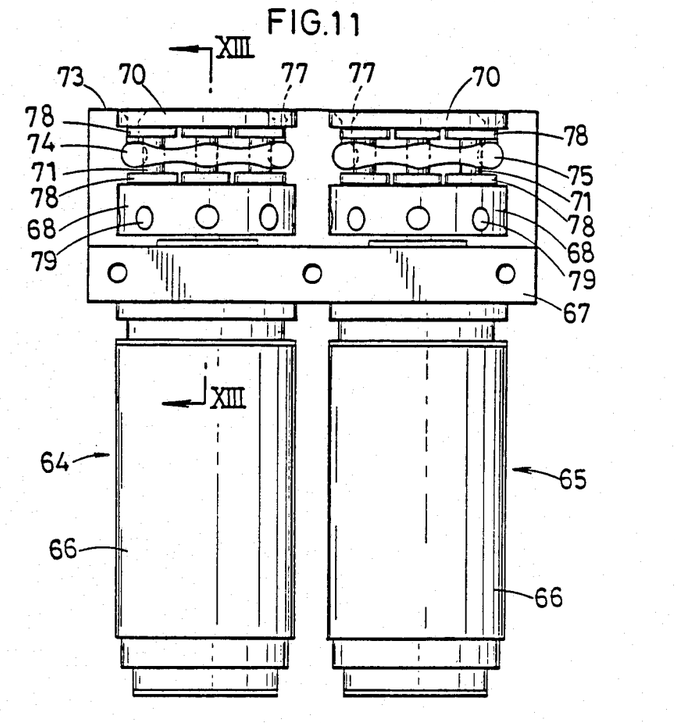
FIG. 11 is a front view showing a modification of the feed pump.
Figure 12:
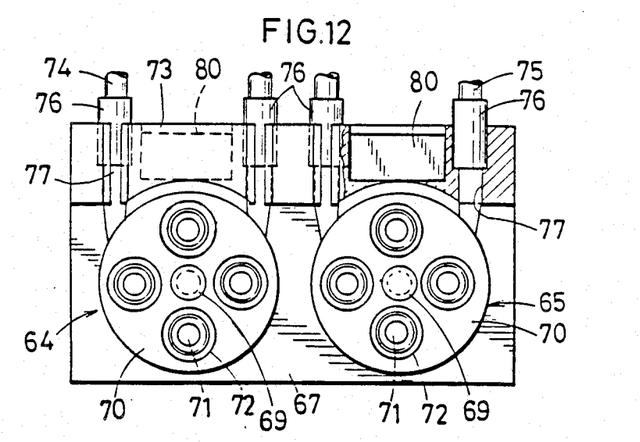
FIG. 12 is a plan view partly broken away and showing the same.
Figure 13:
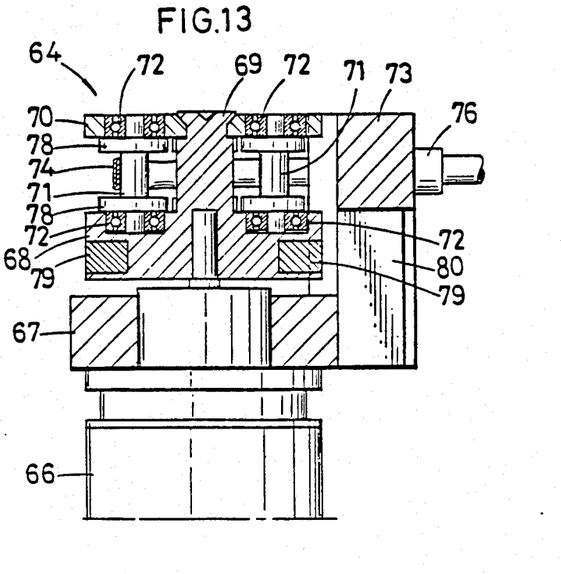
FIG. 13 is an enlarged view in section taken along the line XIII—XIII in FIG. 11.

FIGS. 11 to 13 show an insulin feed pump 64 and a glucagon feed pump 65 which differ from those of the foregoing embodiment. Each of these pumps 64 and 65 has a d.c. motor 66 equipped with a reduction gear and fixed to a horizontal bracket 67 as oriented upward. Coupled to the shaft of the motor 66 is a vertical rotary shaft 69 integral with a roller support 68 in the form of a horizontal circular flange. A disk-like roller support 70 fixed to the upper end of the rotary shaft 69 is opposed to the roller support 68 as spaced apart therefrom by a distance. Four rollers 71 are arranged in parallel with the rotary shaft 69 and equidistantly spaced apart on a circumference centered about the rotary shaft 69. Each roller 71 is rotatably supported at its upper and lower ends by roller bearings 72 mounted on the upper and lower roller supports 70 and 68. An elastic tube holder 73 is fixed to one end of the bracket 67. Intermediate portions of two liquid feeding elastic tubes 74, 75 are reeved, under tension, around some of the rollers 71 of the pumps 64, 65 with use of stoppers 76 secured to the tubes and four stepped grooves 77 formed in the upper side of the holder 73. A flange 78 is formed at the upper and lower ends of each roller 71 integrally therewith for preventing the tube 74 or 75 from zigzagging and slipping off. Eight permanent magnets 79 equidistantly spaced apart are embedded in the outer peripheral side of the roller support 68 of each rotary shaft 69. On the other hand, the portions of the tube holder 73 to be opposed to the permanent magnets 79 are cut out, and rotational angle detectors 80 each comprising a magnetic sensor are fixed to the cutout portions. In this case, every time the rotary shaft 69 of each of the pumps 64, 65 rotates by an amount corresponding to one pitch (45°) of magnet 79, the magnetic sensor of the detector 80 emits a signal. The microcomputer 12 gives a rotational angle instruction in terms of the number of units, one unit being 45°. The rotation of the pumps 64, 65 is controlled based on such instruction values and output signals from the detectors 80. With the exception of the above feature, the modification is the same as the foregoing embodiment.

The front ends of the two liquid feeding elastic tubes, although connected to a single injection needle according to the above embodiment, may be connected to two injection needles individually.

While the injection unit of the above embodiment comprises an insulin container, glucagon container, insulin feed pump and glucagon feed pump to administer insulin or glucagon to the living body, the injection unit may be adapted to inject only one of insulin and glucagon into the living body. Furthermore, glucose may be administered in place of glucagon.

What is claimed is:

1. A micro-feed pump for an artificial pancreas used for medical care comprising:

a roller holder, which is connected to a motor to be rotated, including a pair of disc-like roller supports opposed to each other and having center portions thereof connected to each other in fixed relation;

a plurality of rollers rotatably mounted near the peripheral portion of said roller holder, the opposite ends of each roller being rotatably supported on said roller supports;

an elastic tube having an intermediate portion reeved around said rollers under tension;

a plurality of flanges provided at opposite ends of said rollers for preventing the elastic tube from zigzagging and slipping off;

a plurality of permanent magnets equidistantly embedded in the outer peripheral portion of one of said roller supports;

a fixed pump housing surrounding said roller holder;

a magnetic sensor mounted on said pump housing;

tubular stoppers fixed to an intermediate portion of said elastic tube at two positions, each tubular stopper having an outer diameter larger than that of said tube; and two stepped grooves, each of which is open at its opposite ends and partially open on top, are provided in said pump housing, the elastic tube being secured under tension with the use of said two stoppers and said two stepped grooves, each of said stepped grooves having a tube insertion portion with an inner diameter substantially equal to the outer diameter of said tube, and a stopper insertion portion having an inner diameter substantially equal to the outer diameter of said stopper, both of said portions being essentially circular in section, said tube insertion portion being at the end of said stepped groove nearer said roller holder;

wherein two stoppers are each engaged in fitting relation with a different one of said stopper insertion portions and opposite ends of said intermediate portion of said tube are engaged in fitting relation with each of said tube insertion portions.

* * * * *